United States Patent [19]

Flemer, III

[11] Patent Number: Plant 5,524

[45] Date of Patent: Jul. 30, 1985

[54] *SOPHORA JAPONICA* PRINCETON UPRIGHT

[75] Inventor: William Flemer, III, Princeton, N.J.

[73] Assignee: Treesearch, Kingston, N.J.

[21] Appl. No.: 558,846

[22] Filed: Dec. 7, 1983

[51] Int. Cl.[3] ..... A01H 5/00

[52] U.S. Cl. ..... Plt./51

[58] Field of Search ..... Plt./51

*Primary Examiner*—Robert E. Bagwill

*Attorney, Agent, or Firm*—Frank B. Robb

[57] ABSTRACT

A *Sophora japonica* tree discovered in a block of standard *Sophora japonica* seedlings, specifically in the block of *Sophora japonica* seedlings known as Regent, an unpatented variety, and which my instant variety is distinguished by much more narrow and upright head of branches having a narrow rectilinear crown in outline, more free of cold weather twig die-back than normal seedling grown Sophora trees, resistant to stem cankers, and sparse flowering and fruiting which makes the new variety valuable for street trees grown in paved areas.

2 Drawing Figures

BACKGROUND OF THE INVENTION

As a long time hybridizer, propagator and grower of trees both ornamental and shade, I have trained myself to observe particularly and to select trees from those which are grown in various blocks on property such as that of Princeton Nurseries in Plainsboro Township, N.J., and have chosen certain of the trees observed as desirable to propagate for commercial use and among these is this particular variety of *Sophora japonica* which was observed by me initially growing in a block of open pollinated seedlings of the variety *Sophora japonica* "Regent", grown on property of Princeton Nurseries in Plainsboro Township, N.J. I was particularly attracted to the tree as a seedling by reason of the fact that it was a considerably more narrow tree and has an upright head of branches with a crown of a narrow generally rectangular shape in outline. This particular aspect makes the tree desirable for street trees which would grow in paved areas and certain aspects of the tree itself as will be subsequently described making the same even more attractive from the standpoint of city use.

The parent tree *Sophora japonica* "Regent", an unpatented variety, is much more branching and of wide spread aspect.

DETAILED DESCRIPTION OF THE INVENTION

As previously suggested, the tree of my new variety, having a much more narrow and upright head of branches with a crown of narrow rectilinear shape in outline, suggested that the name of the tree should include an indication of this aspect and I have therefore chosen to call the same *Sophora japonica* "Princeton Upright".

As the name suggests the upright aspect is most noticeable and some of the detailed advantages of the tree as compared with the parent tree, include the noticeably more greater freedom from twig die-back in cold winters which have been experienced since I selected the tree as a new variety for propagation.

This is particularly true as compared with seedling trees grown in the so called usual *Sophora japonica* area in the blocks of Princeton Nurseries with which I have had occasion to compare the instant variety.

It might be noted that this variety when vegetatively propagated by means of bud grafting consistently displays freedom from stem cankers caused by an unidentified fungus of the genus Fusarium, even when trees of the seedling origin in the same block were lightly to heavily injured.

The parent tree of the variety which was discovered by me, and young trees propagated from it which propagation has been effected by bud grafting as before stated, have proved to be sparsely flowering and fruiting in comparison to trees of the same variety, *Sophora japonica* "Regent" grown in the same nursery block, this quality being very desirable for street trees which are to be grown in paved areas.

Under the circumstances it will be understood that I believe this particular variety is desirably to be propagated and will find its place for the purpose of street growth in commerce.

Figure 1:
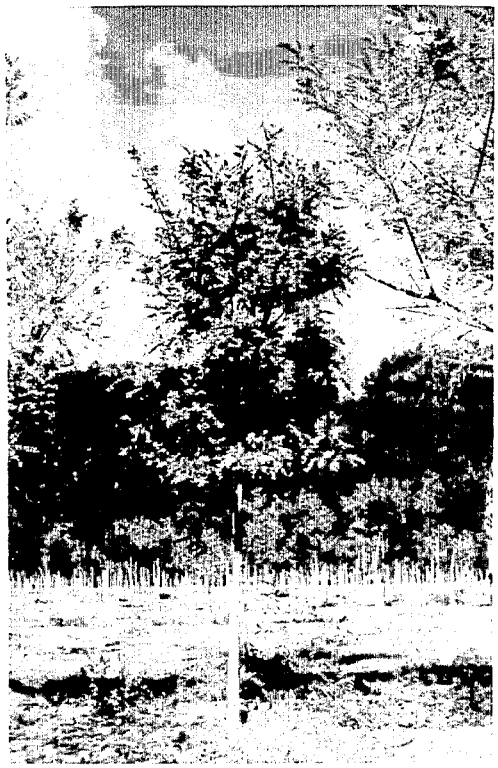

In the accompanying drawing, there is disclosed in FIG. 1 the variety of my discovery, designated "Princeton Upright", and the upright nature of the same and the shape will be observed as disclosed therein.

Figure 2:
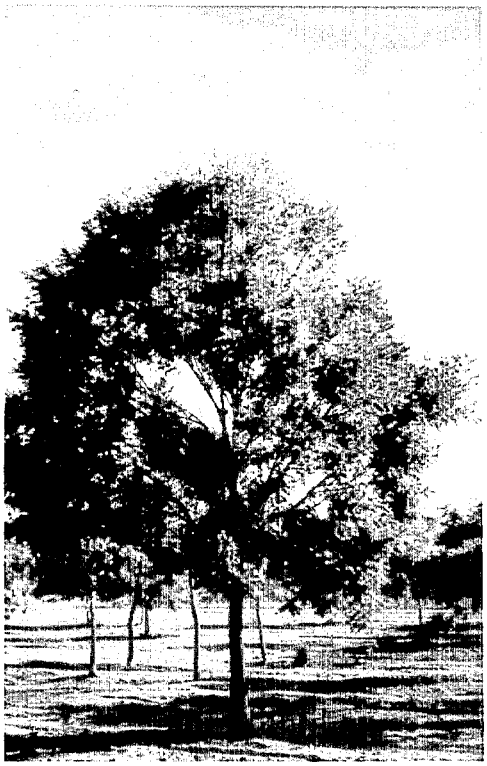

I have chosen to show in FIG. 2 the variety of *Sophora japonica* known as "Regent" for comparison purposes and it will be readily obvious the differences existing therebetween as far as shape is concerned.

The color illustrations of these two figures, are as near to the actual color as is possible to get them in an illustration of this kind, although the colors themselves are not distinctive as between the respective figures, only suggestive of the ultimate colors of the variety as it will appear in commerce.

There is supplied herewith a much more detailed specific description of the variety of my discovery, "Princeton Upright" and the same as to those details distinctive with certain of the color designations which are not necessarily disclosed in the drawing, but are referred to as relating to the Nickerson Color Fan published by Munsell Color Company of Baltimore, Md.

Parentage:

*Seed parent.*—*Sophora japonica* "Regent".

*Pollen parent.*—Unknown.

Tree: Large; upright; tall; dense; hardy.

*Trunk.*—Stocky; smooth.

*Branches.*—Stocky; smooth. Color — 10 GY 4/5 Dark yellowish green. Lenticels — Sparse; Number — Approximately 3 per cm. of length.

*Leaves.*—Quantity — Abundant, compound, 11 to 13 leaflets. Length — 18 to 20 cm. Width — 8 to 10 cm. Shape — Compound, each leaflet 3.5 to 4 cm. long, 2 to 2.2 cm. wide. Color — Upper surface — 10 GY 3/10 Dark grayish green. Lower surface — 7.56 5/8 Strong green. Margin — Smooth edge. Petiole — Short. Glands — None. Stipules — None.

Flower buds: Minute, not significant.

Flowers: Small, compared to other varieties, fragrant. Borne in small, compact, terminal panicles, 800 to 900 flowers per panicle.

*Dates first bloom.*—July 12th to 15th.

*Full bloom.*—July 28th to August 15th.

*Quantity.*—Sparse.

*Size.*—Small; trusses, more compact and smaller in size than trusses of normal seedling populations of *Sophora japonica,* and *Sophora japonica* "Regent".

Petalage:

*Shape of petals.*—Papilionaceous.

*Size of individual flowers.*—Length 1.8 cm.; Width 1.3 cm.

*Color.*—Wings — Greenish yellow, Plate No. 7.5 Y 9/8, with yellow blotch at base. Plate 7.5 Y 8/12. Keel — Pale pink, Plate No. 2.5R 9/3.

Fruits:

*When borne.*—October through November.

*Abundance.*—Sparse.

*Size.*—Borne in short pods 9 to 11 cm. long, 18 cm. wide, 3 to 6 seeds per pod. Color — Strong yellow green 56Y 6/8.

I claim:

1. A new and distinct variety of *Sophora japonica* tree, as herein shown and described, characterized particularly as to novelty by the unique combination of more narrow, upright head of branches having a generally rectilinear crown in outline, resistance to cold winter twig die-back, freedom from stem cankers caused by a fungus of the genus Fusarium though lightly to heavily injured, and sparse flowering and fruiting as compared with standard *Sophora japonica* trees.

* * * * *